United States Patent [19]

Wieser

[11] 4,249,901
[45] Feb. 10, 1981

[54] TOOTH TREATMENT APPARATUS

[75] Inventor: Alfred Wieser, Bad Homburg, Fed. Rep. of Germany

[73] Assignee: Medtronic GmbH, Usingen, Fed. Rep. of Germany

[21] Appl. No.: 952,833

[22] Filed: Oct. 19, 1978

[30] Foreign Application Priority Data

Nov. 24, 1977 [DE] Fed. Rep. of Germany ....... 2752437

[51] Int. Cl.³ .............................................. A61C 1/07
[52] U.S. Cl. .................................... 433/119; 433/98; 433/118
[58] Field of Search ................. 433/119, 118, 100, 99, 433/98, 27; 51/59 SS

[56] References Cited

U.S. PATENT DOCUMENTS

Re. 28,752  3/1976  Balamuth et al. ..................... 433/119
3,213,537  10/1965  Balamuth et al. ..................... 433/98

Primary Examiner—F. Barry Shay
Assistant Examiner—John J. Wilson
Attorney, Agent, or Firm—Thomas R. Morrison

[57] ABSTRACT

A control and drive unit selectively provides either ultrasonic or high frequency energy to a single handle which contains a coil-driven oscillator capable of driving a cleaning or surgical tool. A changeover switch connects the selected signal to the handle and a single control is effective to control either frequency range. A water supply, coupled to the single control, is actuated when a predetermined level of signal power is attained.

10 Claims, 2 Drawing Figures

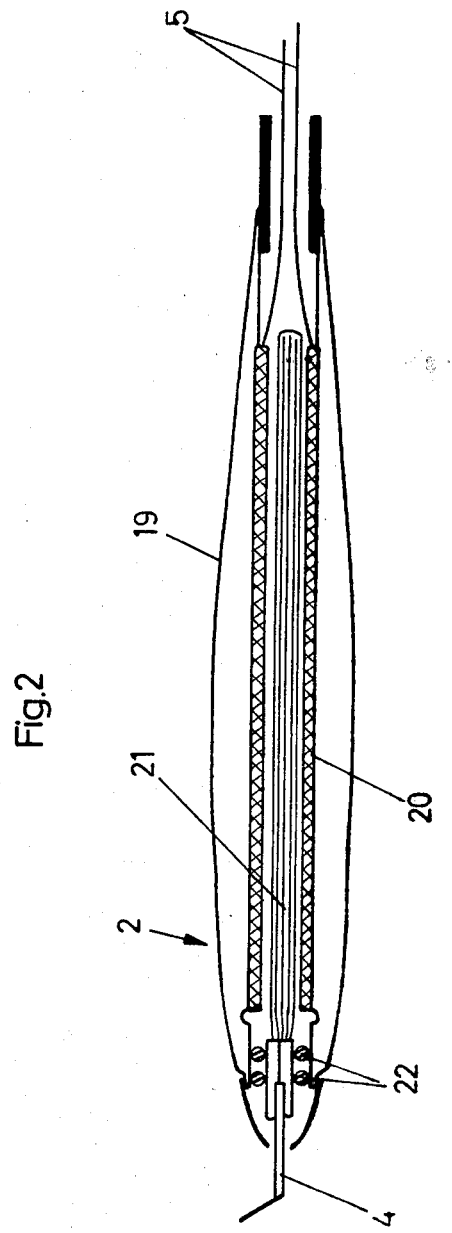

TOOTH TREATMENT APPARATUS

BACKGROUND OF THE INVENTION

The present invention relates to a tooth treatment apparatus with handle arrangement designed for ultrasonic tooth treatment, which is powered by a supply line with an electrical signal of a control and/or drive unit.

Ultrasonic tooth treatment devices are known and they are used in dental practice for example for removing of deposits on teeth. In addition, high frequency surgical devices for carrying out surgery or treatment are also known. The ultrasonic tooth treatment devices as well as the high frequency surgical devices involve two different physical instruments, in which each instrument consists of a handle arrangement and, for each device type, specific control and drive units. The handle arrangements, which, in the case of ultrasonic tooth treatment instruments accommodate an electricomechanical converter with which a tool is connected and which in the instruments for high frequency surgery have special electrodes, are connected by supply lines to the associated control and drive units.

If a tooth treatment arrangement incorporates both types of instruments (ultrasonic tooth treatment instrument and high frequency surgical instrument), which is nowadays required without exception, then it is necessary to have two separate control and driving units, associated with the double expenditure for the accommodation area and material. It could be considered to accommodate both control and driving units into a common housing, this, however, owing to the associated winding arrangements for the supply lines required for each instrument group of different manually operated instruments, requires a minimum space which is largely determined by the winding arrangement.

SUMMARY OF THE INVENTION

The object of the present invention is to avoid the disadvantages of the known instruments and to provide a tooth treatment instrument which, in spite of the versatility in application, requires very little accommodation space.

For the solution of this task, a tooth treatment instrument of the above described kind is designed according to the invention so that on changeover of the control and/or drive unit the electrical signal is optionally a signal with a frequency in the ultrasonic range or it is a high frequency signal.

By the dual purpose handle arrangement designed for conventional ultrasonic tooth treatment as well as for high frequency surgery, a considerable saving in costs and in accommodation space is achieved. The optional control of the handle arrangement designed for the ultrasonic tooth treatment with an electrical high frequency signal converts this handle arrangement into a high frequency manually operated instrument, in which it is only necessary to replace the ultrasonic tooth treatment tool specified for the handle arrangement by the electrodes usually used for the high frequency treatment or for high frequency surgery.

By means of the invention it becomes possible to use a single handle arrangement for ultrasonic tooth treatment and for high frequency treatment, so that only a single winding arrangement is necessary for the connection line for a single handle arrangement. This arrangement ensures especially a considerable saving of space and accommodation.

A further advantage of the instrument according to the invention is that the already existing tooth treatment instruments which are provided with one or more ultrasonic handle arrangements can be re-equipped. The tooth treatment instruments do not have, as a rule, any space for an additionally provided high frequency instrument or apparatus but have sufficient space for accommodating a special generator for generating high frequency signals and also space for the means necessary for changeover switching.

In the instrument according to the invention the handle arrangement as well as the electrodes, which are used as a tool for high frequency treatment (high frequency surgery) can be designed so that a supply of cooling or flushing water may be delivered to the operation point, by means of which it is possible to carry out, for example, a cutting in wet conditions with coolant supply which was not possible previously with known high frequency surgery instruments. The electrodes or the tool with electrodes are in this case provided with a water outlet nozzle so that the water jet is directed on the operation point. Any other suitable coolant or a substance, which also contains additionally medically effective substances, can, of course, be used instead of water.

According to a preferred embodiment of the invention, means are provided whereby the performance of the handle arrangement can be adjusted for ultrasonic tooth treatment and/or for high frequency treatment, in which the cooling water or the coolant supply is controlled on the handle arrangement preferably in such a manner that a coolant flow follows only upwards of a certain, specified power output.

BRIEF DESCRIPTION OF THE DRAWINGS

FIG. 2 shows a cross section of a handle arrangement.

DETAILED DESCRIPTION OF THE PREFERRED EMBODIMENT

Figure 1:
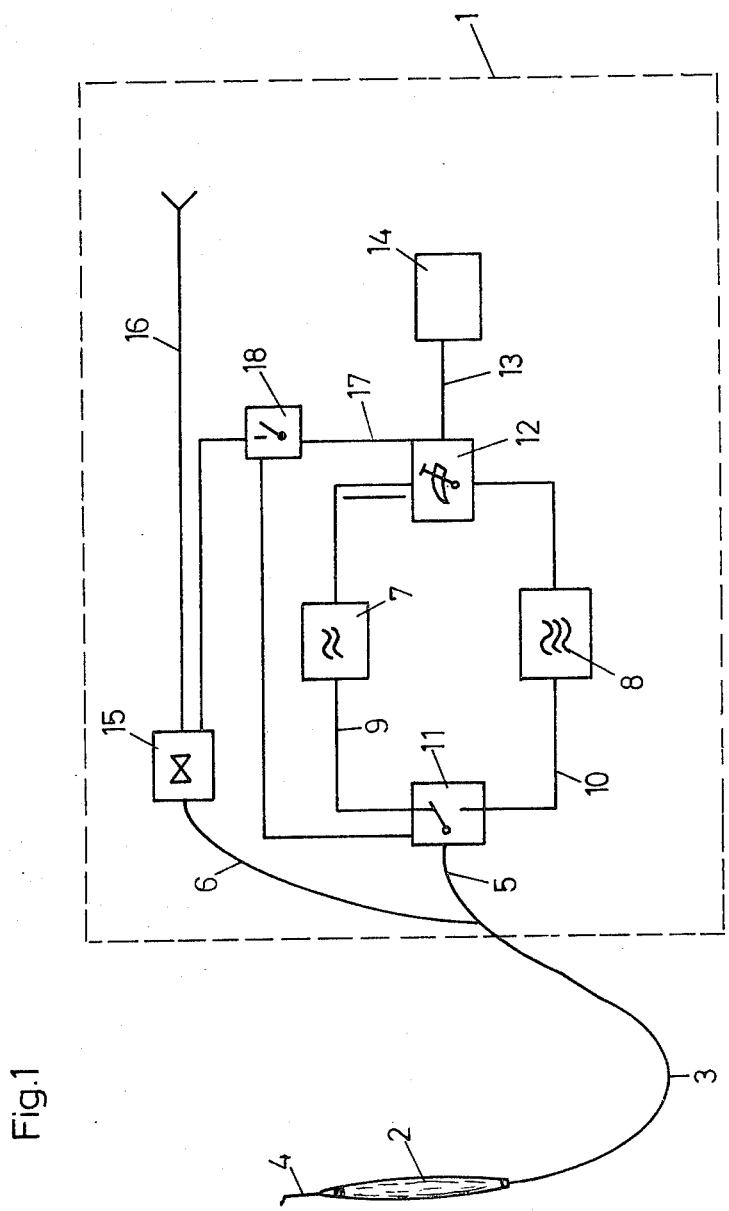
FIG. 1 shows a block diagram of a dental instrument according to the present invention.

The invention is described in greater detail below by means of the Figures and an embodiment example. FIG. 1 shows a block circuit diagram of a dental treatment instrument according to the invention consisting of the control and drive unit 1 as well as of the handle arrangement 2 designed for ultrasonic treatment, which handle arrangement has an electromechanical converter, for example a magnetostrictive converter (not shown in FIG. 1) and which is connected by a supply line 3 with the control and drive unit 1. On the handle arrangement 2 or on the mechanical output of the electromechanical converter specified in this handle arrangement is fastened a tool 4 which can be removed or replaced, whereby this tool 4 is, depending on the application of the treatment instrument, either an ultrasonic tool, for example for removing of tooth deposits, or a high frequency surgery tool.

In addition to the electrical cables 5, preferably two electrical cables for the actuation of the electromechanical converter in the handle arrangement 2, the supply line 3 incorporates also a flexible hose 6, by means of which the handle arrangement can be supplied with cooling or flushing water. The end of the hose 6 is connected to at least one opening or one nozzle, which is arranged on tool 4. The use of the water supplied by the hose 6 is advantageous especially also on using the instrument for high frequency surgery, because in this case, for example, cutting under wet conditions is possible. In the case where the tool 4 is used for high frequency surgery the water outlet nozzle is arranged in relation to the electrodes of this tool so that the water jet is directed on the point of operation.

The control and drive unit 1 incorporates two electrical generators 7 and 8, of which the generator 7 generates an electrical signal whose frequency is situated within the ultrasonic range, while the generator 8 supplies a high frequency signal at its output. The generator 7 is in this case, for example, a sine wave or pulse generator, while the generator 8 is preferably a sine wave generator. The outputs of the generators 7 or 8 are connected by the cables 9 or 10 to a changeover arrangement 11, which is represented in the Figure for simplicity of representation as a simple changeover switch and by means of which the electrical cable 5 end furthest from the handle arrangement 2 can be connected optionally to the generator 7 or to the generator 8.

The changeover arrangement 11 in this case is designed so that when the electrical connection cable 5 is connected to the generator 7 then the individual wires of the electrical connection cable 5 are connected with the associated output terminal of the generator 7, i.e. in the case of two individual wires connected to a given single terminal of the magnetostrictive converter in the handle arrangement 2 within the electrical connection cable 5 these individual wires are connected to both output terminals of the generator 7. On connecting the handle arrangement 2 or the electrical connecting cable 5 to the generator 8 all individual wires of the electrical connection cable 5 are connected in parallel and connected with a common output terminal of the generator 8.

The changeover arrangement 11 is formed preferably by a corresponding relay switch; it is, of course, also possible to build the changeover arrangement with semiconductor components or with semiconductor switches such as transistors, thyristors etc.

For the control of the output performance of the generators 7 and 8 there is specified, for the embodiment represented here, a regulating arrangement 12 common to both generators, in which this regulating arrangement in the simplest case varies the supply voltage of the generators 8 and 9 or one part of these generators according to the required output performance. For this purpose the regulating arrangement 12 is connected by a conductor 13 to the supply voltage source 14.

If the water supply by the hose 6 to the handle arrangement 2 is to be controlled in such a manner that only on using this handle arrangement as high frequency instrument and also if, and only if a certain power level of the generator 8 is exceeded, a cooling or flushing water outlet on the nozzle of the handle arrangement 2 or of the tool 4 will occur, then the regulating arrangement 12 has further means which, upwards of a certain position of the regulator of the regulating arrangement 12, corresponding to a specified power level, supply a control voltage for opening a valve 15, the latter valve being situated within the connection between the hose 6 and a cooling or flushing water supply line 16. This means for switching of the valve 15 is formed in the simplest case by a contactor within the regulating arrangement 12 which, upwards of a certain output performance of the generator 8, will close an electrical current circuit. In the control line 17 between the valve 5 and the regulator arrangement 12 is arranged a switch 18, which closes only if by the changeover arrangement 11 the connection is established between the handle arrangement 2 and the generator 8. This switch 18 can be either a contactor or a relay forming the changeover arrangement 11 or, however, the switch 18 is formed by a second electrically or electronically actuated switch, whereby this switch is then actuated by the changeover arrangement 11. Of course it is also possible to link the switch 18 by mechanical means with a switch which is not described in detail, by which follows the actuation of the changeover arrangement 11.

FIG. 2 shows a diagrammatic representation of a longitudinal cross section through the handle arrangement 2 as well as through the electromechanical converter accommodated by this handle arrangement. The handle arrangement 2 consists of an external, long and slender housing 19 into which is arranged a cylindrical coil 20, which, together with the oscillator 21 projecting into the coil cavity, forms the electromechanical converter. The oscillator 21 is supported, so that it can move, on its one end which projects over the coil 20, in which this support is in the simplest case formed by ring shaped elements 22 made from plastic material, for example from rubber. The tool 4 is screwed into the oscillator 21 end facing away from the coil 20. In the representation selected for FIG. 2 the tool 4 is an ultrasonic tooth treatment tool. For the high frequency treatment this tool 4 can be exchanged for a corresponding electrode, which is then screwed into the oscillator 21. Of course it is also possible to connect the oscillator firmly with the associated tool or with the associated electrode, whereby the whole oscillator together with the tool is then replaced by pulling out of the housing 19 or coil 20 or by pushing into the housing 19 and into the coil 20.

The coil 20 has two connecting cables 5 which are connected, when the handle arrangement 2 is used for an ultrasonic tooth treatment, by the cable 3 in the usual manner with the two terminals of the corresponding generator 7 in such a manner that the driving or control signal will reach via one conductor to the coil 20 and this signal is fed back via the other conductor to the generator 7.

In the case of a high frequency treatment both cables 5 are connected in parallel by corresponding changeover of the changeover arrangement 11. The coil 20 acts then in this case together with the oscillator 21 which consists of a stack of thin steel sheets or of some other suitable metal alloy, in the manner of a tubular capacitor, in which the high frequency voltage supplied by a parallel connected cable 5 is transmitted from the coil to the oscillator and from the latter to the electrode projecting beyond the housing 19 and used as a tool.

The invention was explained above by an embodiment example. It is understood that modification as well as variations are possible, without departure from the idea of the invention.

I claim:

1. Tooth treatment instrument comprising:
   (a) a handle arrangement;
   (b) vibratory transducer means in said handle arrangement for receiving said electrical signal and for generating an oscillatory mechanical output;

(c) first signal generator means for generating an ultrasonic electrical signal;

(d) second signal generating means for generating a high frequency electrical signal; and (e) changeover means for selectively connecting the signal from the first or second generator means to the handle arrangement.

2. Tooth treatment instrument according to claim 1 further comprising water supply means for supplying water to said handle arrangement and comprising water control means, said water control means being effective above a certain power level of the high frequency signal, to switch on the water supply means.

3. Tooth treatment instrument according to claim 2 further comprising a single regulating arrangement for controlling the power level of the high frequency signal and for controlling the water supply.

4. Tooth treatment instrument according to the claim 3 wherein the regulating arrangement, on adjusting a certain power level for the high frequency signal, is effective to supply a control signal for opening a valve in the water supply system.

5. Tooth treatment instrument according to claim 1, further comprising means for detachably attaching a tool to said vibratory transducer means.

6. Tooth treatment instrument according to claim 5, further comprising water supply means for supplying water to said handle arrangement and water control, said means for detachably attaching a tool being operative to attach a high frequency surgical tool having a water outlet nozzle means thereon to said handle arrangement, said water outlet nozzle means being connected with said water supply means, and being effective to direct a water jet onto an operating point.

7. Tooth treatment instrument comprising:
(a) a handle arrangement containing a vibratory transducer including a coil;
(b) first signal generator means for generating an ultrasonic electrical signal;
(c) second signal generator means for generating a high frequency electrical signal;
(d) changeover means for selectively connecting said ultrasonic signal or said high frequency signal to said coil;
(e) regulating means for controlling whichever one of said first and second signal generator means is connected to said coil;
(f) means for detachably attaching a tool to said oscillator;
(g) water supply means for supplying water to said tool; and
(h) said regulating means also being effective for controlling said water supply means.

8. Tooth treatment instrument according to claim 7 or 1 wherein the high frequency signal has a frequency of at least 1 MHz.

9. Tooth treatment instrument according to the claim 7 or 1 wherein the changeover means is a relay changeover switch.

10. Tooth treatment instrument according to claim 7 or 1 wherein said changeover means is effective to connect said high frequency signal in parallel from one output terminal of a generator supplying a high frequency signal to all input terminals of said handle arrangement.

* * * * *